United States Patent [19]

Moore

[11] Patent Number: 4,639,455

[45] Date of Patent: Jan. 27, 1987

[54] MEANS OF AIDING IN THE PREVENTION OF SUDDEN INFANT DEATH SYNDROME

[75] Inventor: Luana Moore, Miami Beach, Fla.

[73] Assignee: Key Pharmaceuticals, Inc., Miami, Fla.

[21] Appl. No.: 657,096

[22] Filed: Oct. 2, 1984

[51] Int. Cl.$^4$ .............................................. A61K 31/41
[52] U.S. Cl. ..................................... 514/282; 514/823
[58] Field of Search ................................ 514/282, 823

[56] References Cited

U.S. PATENT DOCUMENTS 3,814,768 6/1974 Fishman .............................. 514/823

Primary Examiner—Nicky Chan
Assistant Examiner—John W. Rollins, Jr.
Attorney, Agent, or Firm—Anita W. Magatti; Gerald S. Rosen; Stephen I. Miller

[57] ABSTRACT

A means of aiding in the prevention of Sudden Infant Death Syndrome (SIDS) is disclosed. The means comprises administering a pharmaceutically effective amount of the drug 6-methylene-6-desoxy-N-cylopryplymethyl-14-hydroxydihydronormorphone to an infant determined to be susceptible to SIDS. The drug is preferably administered bi-daily via the GI tract. The drug attaches to the nerve receptor sites responsible for the actuation of respiration thus blocking the attachment of endogenous endorphins which, if present in high levels, prevents such actuation resulting in apnea and SIDS. A suppository containing the drug for use in carrying out the method is also disclosed.

7 Claims, No Drawings

MEANS OF AIDING IN THE PREVENTION OF SUDDEN INFANT DEATH SYNDROME

FIELD OF THE INVENTION

The present invention relates to the field of means for aiding in the prevention of Sudden Infant Death Syndrome (hereinafter SIDS). More specifically, the invention relates to administering the drug 6-methylene-6-desoxy-N-cyclopropylmethyl-14-hydroxydihydronormorphone to an infant determined to be susceptible to SIDS and to an anal suppository containing such a drug.

BACKGROUND OF THE INVENTION

Sudden Infant Death Syndrome (SIDS), also called "Crib Death", can be defined as the sudden death of any infant which is unexpected according to history and in which a post-mortem fails to demonstrate an adequate cause of death. Although the death might be unexpected according to the infant's history as examined in a conventional manner a SIDS death might have been predictable or at least determined to be more probable with that specific infant due to its history. For example, premature infants, low birth weight infants and those with respiratory distress syndrome are more likely to suffer a SIDS death than other infants. Another group of infants more likely to be susceptible to a SIDS death would be the "Near-Miss" infants, i.e. those who have been successfully revived after respiration ceased. A number of other factors are known to be associated with an increased likelihood of suffering a SIDS death.

In an attempt to reduce the number of SIDS deaths, attempts have been made to identify those infants who would be more likely to suffer a SIDS death. After identifying such infants, the parents are notified and mechanical devices can be attached to the infant. These mechanical devices monitor the respiration and/or heartbeat of the infant and actuate an alarm when respiration and/or heartbeat ceases. The parents can respond to the alarm and revive the infant. Such devices are advantageous in that they do not require the administration of any drugs to the infant. However, they are undesirable in that they may fail due to mechanical malfunction or an interruption of their power supply. Further, individuals might fail to respond to the alarm or fail to respond fast enough in order to revive the infant. Perhaps most importantly, such devices do nothing to prevent respiratory arrest and respiratory arrest for even a short period of time can of course cause brain damage.

Due to the deficiencies with utilizing such systems and in an effort to advance science in this area a substantial number of studies have been done with respect to the mechanisms within the body controlling respiration. More specifically, studies have been done with respect to the causes for interrupting or depressing respiration. Recent studies have indicated that beta-endorphins cause depression of ventilatory regulation ($CO_2$-response test). (see Moss, I. R., and Freedman, E., Beta-Endorphins: "Effects on Respiratory Regulations". Life Science, 23:1271, 1978.) The study showed that these beta-endorphins depress the spontaneous discharge of respiratory center neurons and that the depressant effect on response to $CO_2$ are temporarily reversed by the injection of naloxone. (Cdenavit-saubie, m.Champagnat, J., and Zieglgansberger, W: "Effects on opioids and Methionine-Enkephalin on pontine and Bulbar respiratory neurons of the cat". Brain res. 155:55, 1978.) The administration of naloxone invariably stimulates breathing in previously apneic subjects and also facilitates the breathing response to $CO_2$ both by decreasing estimated $CO_2$ threshold and increasing calculated fetal sensitivity to $CO_2$. Naloxone is an opiate antagonist and thus the stimulation caused by administering naloxone is created by the displacement of endogenous opioids from their natural receptor sights. Thus the administration of naloxone blocks the action of endorphins which participate in the physiological suppression of respiratory control in fetal life.

Although naloxone can be useful in blocking endogenous endorphins and thus aid in the prevention of respiratory suppression or arrest, naloxone has a relatively short half-life and is substantially metabolized on the first pass through the liver. Due to its relatively short half-life (approximately 35-45 minutes) the drug must be administered frequently in order to have a continuous effect on preventing respiratory suppression or arrest. Since the drug is substantially metabolized on the first pass through the liver to a metabolite which is ineffective with respect to blocking endogenous endorphins, the drug can not generally be effectively administered via the GI tract. The need for frequent re-dosing and intravenous administration makes the use of naloxone in preventing SIDS impractical.

SUMMARY OF THE INVENTION

The present invention eliminates the disadvantages of the prior art by providing a means for aiding in the prevention of SIDS which can be administered in bi-daily doses via a number of different routes including the GI tract. The invention comprises administering a pharmaceutically effective amount of 6-methylene-6-desoxy-N-cyclopropylmethyl-14-hydroxydihydronormorphone to an infant determined to be susceptible to SIDS. The 6-methylene-6-desoxy-N-cyclopropylmethyl-14-hydroxydihydronormorphone attaches to nerve receptor sites responsible for the actuation of respiration. The attachment of the 6-methylene-6-desoxy-N-cyclopropylmethyl-14-hydroxydihydronormorphone blocks the attachment of endogenous endorphins. Such endorphins can, if present in high levels, prevent such actuation and thus result in the suppression or arrest of respiration. The 6-methylene-6-desoxy-N-cyclopropylmethyl-14-hydroxydihydronormorphone has a long half-life on the order of about 10 to 13 hours. Although it is eventually metabolized by the liver to glucuronide, due to its long half-life it can be administered in bi-daily doses and still maintain an effective plasma blood level. Since the drug is not substantially metabolized on the first pass through the liver it can be administered via the GI tract (orally or anally) and still provide the results desired.

It is a primary object of the present invention to provide a means of aiding in the prevention of Sudden Infant Death Syndrome.

Another object of the invention is to provide such a means which includes administering a pharmaceutically effective amount of 6-methylene-6-desoxy-N-cyclopropylmethyl-14-hydroxydihydronormorphone to an infant determined to be susceptible to SIDS.

Yet another object of the invention is to administer 6-methylene-6-desoxy-N-cyclopropylmethyl-14-hydroxydihydronormorphone via the GI tract.

Still another object is to provide such a means whereby the 6-methylene-6-desoxy-N-cyclopropylmethyl-14-hydroxydihydronormorphone is administered orally in bi-daily doses.

Yet another object of the invention is to provide such a means whereby 6-methylene-6-desoxy-N-cylopropyl-methyl-14-hydroxydihydronormorphone is administered orally in bi-daily amounts in the range of 0.01 mg per kilogram to 0.5 mg per kilogram of body weight.

Another object is to provide an anal suppository containing 6-methylene-6-desoxy-N-cyclopropylmethyl-14-hydroxydihydronormorphone which can be administered to an infant.

These and other objects of the invention will become apparent to one skilled in the art upon reading the present disclosure.

DETAILED DESCRIPTION OF THE INVENTION

The drug utilized in order to provide the means of the present invention is 6-methylene-6-desoxy-N-cyclopropylmethyl- 14-hydroxydihydronormorphone which is also known as nalmefene. With respect to the present invention, the use of the term 6-methylene-6-desoxy-N-cyclopropylmethyl-14-hydroxydihydronormorphone or nalmefene means the free base of nalmefene, the acid as well as all of the pharmaceutically acceptable salts. In accordance with the present invention the hydrochloride salt is particularly preferred. The hydrochloride salt is a white powder having the molecular formula $C_{21}H_{25}NO_3:HCL$: a molecular mass of 375.896 and a melting point of 200° C. nalmefene has the following chemical structure:

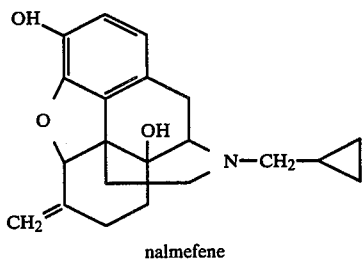

nalmefene

The chemical structure of nalmefene is similar to naloxone and naltrexone. The chemical structure of naloxone is:

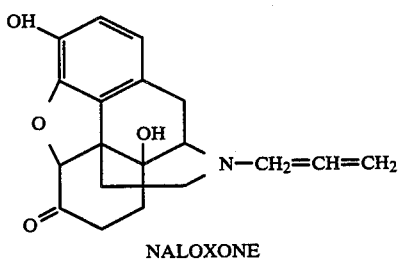

NALOXONE

The chemical structure of naltrexone is as follows:

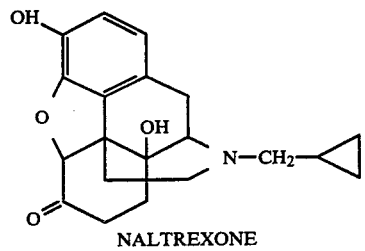

NALTREXONE

Details with respect to naloxone can be found within U.S. Pat. No. 3,254,088 and The Merck Index, 10th Edition, entry #6208. Details with respect to naltrexone can be found in U.S. Pat. No. 3,332,950 and within the Merk Index, 10th edition, entry #6209. Additional details with respect to how to make nalmefene which can be used in connection with the present invention are disclosed within U.S. Pat. No. 3,814,768 (incorporated herein by reference to disclose how to make nalmefene).

By comparing the chemical structures of naloxone, naltrexone and nalmefene it can be seen that nalmefene differs from the other two with respect to the methylene group at the 6 position. It is believed that the presence of this group is responsible for providing the enhanced oral bio-availability of nalmefene as compared with the other two drugs when administered via the GI tract. All three of the drugs are known to act as antagonists with respect to narcotics.

Since all three drugs can be utilized as narcotic antagonists all three drugs could conceivably be utilized to aid in the prevention of SIDS by blocking receptor sites and thus prevent endogenous endorphins from suppressing or arresting respiration. However, as indicated above, naloxone and naltrexone are substantially metabolized on the the first pass through the liver and the metabolite of these drugs is not effective in blocking receptor sites for endogenous endorphins.

Naloxone, which is an opiate antagonist has been shown, when administered in doses of 0.4 and 4.0 mgs/kilogram to markedly reduce the duration of primary apnea in asphyxiated newborns. (See "Naloxone decreases the duration of primary apnea with neonatal asphyxia", Chernick et. al, Pedia. Res. 14: 357–359 1980). However, the same effect was not seen at a dose of 0.04 mg/kg. However, with respect to blocking receptor sites nalmefene has been found to be approximately twelve times more potent than naloxone.

Due to the greater potency of nalmefene with respect to naloxone, the contemplated dosage of nalmefene in accordance with the present invention is in the range of about 0.05 mg/kg to about 0.5 mg/kg. When nalmefene is in a suppository some of the drug may remain unabsorbed. Accordingly, a nalmefene suppository should contain about 0.05 to 1.0 mg of nalmefene which could be administered bi-daily to a 1 kg infant. Correspondingly higher concentrations of nalmefene could be included in suppositories for infants of 2, 3, 4 and 5 kilograms or more. Alternatively, correspondingly greater numbers of such suppositories could be administered, e.g. administer 3 suppositories containing 1.0 mg or one suppository containing 3 mg nalmefene to a 3 kilogram infant.

The dosage of nalmefene may be administered to the infant in any manner which allows for the infusion of the nalmefene into the systemic cardiovascular system. It is only necessary that the nalmefene be allowed to reach receptor sites in the brain which are connected with respiration. Accordingly, the nalmefene may be administered intravenously, orally, or via an anal suppository. Since drugs like naloxone and naltrexone are substantially metabolized on the first pass through the liver, their bio-availability is substantially reduced when they are administered orally or anally. Accordingly, naloxone and naltrexone are generally administered intravenously. Although intravenous administration allows for the drug to enter the systemic cardiovascular system, such a means of administration generally requires the aid of hospital personnel thus adding to the expense of administration. Furthermore, such a means of administration is not normally available in the home and can be painful if required over a long period of time.

A preferred embodiment of the present invention is administration of nalmefene via the GI tract. Such means of administration eliminates the pain, expense and inconvenience of intravenous administration. Since nalmefene is not substantially metabolized on the first pass through the liver it is possible to administer nalmefene via an oral formulation. Administration via the GI tract includes administration from an anal suppository. The use of anal suppositories to administer nalmefene to infants determined to be susceptible to SIDS is particularly preferred in that such infants are often premature and thus inept with respect to swallowing. Accordingly, the particularly preferred embodiments of the present invention involve nalmefene in the form of an anal suppository and administering nalmefene via such an anal suppository.

When a suppository formulation is used, the carrier material must have a melting point sufficiently high as to maintain its structural integrity at room temperature, but sufficiently low so as to "melt" or "dissolve" slowly at body temperature and thus release the nalmefene. Useful carrier materials include cocoa butter, glycerinated gelatin, hydrogenated vegetable oils, mixtures of polyethylene glycols of various molecular weights, fatty acid esters of such polyethylene glycols and various combinations of these materials. (see Remington's Textbook of Pharmaceutical Science 16th ed., page 153.)

When the nalmefene is administered via a suppository, the nalmefene enters the body via the rectum. Since return of blood from the rectum and anal canal is via two systems, the nalmefene enters the body in two different ways. More specifically, the nalmefene absorbed through the rectum is absorbed via the superior rectal (hemorrhoidal) vein which drains the rectum and upper part of the anal cavity into the portal system via the inferior mesenteric vein. The middle rectal veins primarily drain the lower part of the rectum and the upper part of the anal canal. These veins accompany the middle rectal arteries and terminate in the internal iliac veins. The inferior rectal veins, following the corresponding arteries, drain the lower part of the anal canal via the internal pudendal veins which empty into the internal iliac veins. The superior, middle and inferior rectal veins converge to form the internal rectal (hemorrhoidal) plexus in the submucosa of the columns of Morgagni.

Accordingly, when nalmefene is administered to an infant via a suppository, some of the nalmefene will enter the body via the portal circulation which causes the drug to pass directly to the liver before passing into the systemic circulation. Another portion of the drug will enter directly into the systemic cardiovascular system. In general, the higher the suppository is pushed into the rectum, the greater the exposure to the portal circulation via the superior rectal veins. Since nalmefene is not substantially metabolized on the first pass through the liver, the precise positioning of the suppository in the infant is not critical. The drug may enter the body via the portal circulation or the systemic cardiovascular circulatory system and be substantially equally effective.

The following examples are given for the purpose of illustration of this invention and are not intended as limitations thereof. These examples are offered merely to show how a suppository formulation as encompassed by the present invention might be produced. Parts throughout are by weight unless indicated otherwise.

EXAMPLE 1

The base carrier formulation can be composed by mixing together equal weight amounts of polyethylene glycols having the following average molecular weights: 300; 400; 1540, 4000 and 6000. Mix the polyethylene glycols of various molecular weights to obtain a uniform consistent mixture of each polyethylene, add 1 gram of nalmefene per 1000 grams of mixture and thoroughly blend the nalmefene throughout the mixture until the nalmefene is evenly distributed throughout all parts of the polyethylene glycol. The mixing should preferably be carried out at a temperature of about 60° centigrade which allows the polyethylene glycol to remain in a substantially liquid state. When the mixture becomes homogeneous, it can be poured into substantially bullet shape molds capable of containing 1 gram of the homogeneous mixture. The mixture is then allowed to solidify at about 20° centigrade. After solidification, the bullet shaped suppositories can be removed from the molds and packaged. Each 1 gram bullet shaped suppository will contain 1 milligram of nalmefene and is suitable for administration to a 1 kilogram infant on a bi-daily basis.

EXAMPLE 2-5

Suppository formulations in accordance with examples 2-5 can be produced by following the same procedure as in example 1 except that 2, 3, 4 and 5 grams of nalmefene is added to the polyethylene glycol per 1 kilogram of polyethylene glycol. After formation of the bullet shaped suppositories, each suppository will contain, respectively, 2, 3, 4 and 5 milligrams of nalmefene. These suppositories are respectively suitable for administration to infants having a size of 2, 3, 4 and 5 kilograms on a bi-daily basis.

EXAMPLE 6

Equal weight amounts of polyethylene glycols having various molecular weights, as in example 1, can be blended together in a homogeneous mixture at about 60° centigrade. The homogeneous mixture of polyethylene glycols can than be combined with an equal weight amount of cocoa butter and blended together with the cocoa butter to form a homogeneous mixture at a temperature of about 60° centigrade. A fraction equal to about 1/10 of the homogeneous mixture can then be extracted for combination with the active ingredient nalmefene. The extracted fraction is blended thoroughly with nalmefene in a ratio of 1 part by weight nalmefene to 100 parts by weight of mixture of cocoa butter and polyethylene glycol. While maintaining both mixtures at about 60° centigrade with stirring the mixture containing the nalmefene can be recombined with the original cocoa butter and polyethylene glycol mixture and thoroughly blended in order to insure that the nalmefene is evenly distributed throughout the mixture at a concentration of 1 part by weight nalmefene per 1000 part by weight of the total mixture. The mixture containing the nalmefene is then placed into molds while the mixture remains in a substantially liquid state. The molds can be sized so as to contain about 1 gram of the mixture. The molds can be allowed to cool at about 20° centigrade to form a substantially solid suppository formulation which will contain 1 milligram of nalmefene. The suppositories are suitable for bi-daily administration to a 1 kilogram infant found to be susceptible to SIDS.

EXAMPLES 7-10

The polyethylene glycol blend and cocoa butter mixture as in example 6 can be used to prepare suppositories containing higher concentrations of nalmefene by adding nalmefene in the manner indicated in example 6 in amounts of 2, 3, 4 and 5 grams of nalmefene per 100 grams of mixture at 60° centigrade. This concentrated mixture can then be recombined with the original cocoa butter and polyethylene glycol mixture as indicated in example 6 to provide a concentration of nalmefene in the amount of 2, 3, 4 and 5 grams per 1000 grams of mixture. Bullet shape suppositories can then be formed as indicated in example 6 and administered to infants having a body weight of 2, 3, 4 and 5 kilograms respectively in order to aid in the prevention of SIDS.

EXAMPLES 11-20

Suppository formulations can be provided in the same manner as indicated in examples 1-10 above. However, ascorbic acid is added to each of the formulations in the amount of 40 parts by weight based on 1000 parts by weight of the carrier in order to act as a mucous membrane penetration enhancer.

EXAMPLE 21

Eighty parts by weight of a polyethylene glycol blend having an average molecular weight of 3000 can be combined together with 10 parts by weight of cocoa butter and 10 parts by weight of polyethylene oxide having a molecular weight of 5 million. The three components can be mixed together at about 60° centigrade until a homogeneous carrier mixture is obtained. A small portion of the mixture can be extracted and blended together with nalmefene in an amount of 1 part by weight of nalmefene per 1000 parts by weight of the total mixture. The extracted portion mixed with the nalmefene is to be returned to the original mixture to provide a homogeneous blend containing 1 part of nalmefene per 1000 parts by weight of the total mixture. Stirring should be continually carried out to insure that the nalmefene is evenly distributed throughout the mixture. While keeping the mixture at a temperature sufficiently high to keep it in a substantially liquid state, it can be put into suppository containers having a size such that each suppository container mold is capable of including 1 gram of the mixture. The molds are then cooled to approximately 20° centigrade in order to form a solid suppository which can then be removed from the mold. Each suppository contains 1 milligram of nalmefene which can be administered on a bi-daily basis to a 1 kilogram infant in order to aid in the prevention of SIDS.

EXAMPLES 22-25

The same procedure as indicated in example 21 above can be carried out with the exception of adding 2, 3, 4 and 5 parts by weight of nalmefene per 1000 parts by weight of the total mixture to provide 1 gram suppositories containing 2, 3, 4 and 5 milligrams of nalmefene which can be administered on a bi-daily basis to 2, 3, 4 and 5 kilogram infants in order to aid in the prevention of SIDS.

The above examples 1-25 are given merely as possible formulations to be considered in providing a suppository which would include nalmefene as an active ingredient. Numerous other formulations will be apparent to those skilled in the art. It should be noted that the use of suppositories for administering nalmefene for the prevention of SIDS is considered to be particularly desirable for a number of reasons. Firstly, premature infants are often inept with respect to swallowing. Any swallowing difficulties are, of course, avoided by administering the drug via a rectal suppository. Although nalmefene itself is not known to cause gastrointestinal disorders, if administered orally, to an infant, the drug could be regurgitated and thus not be absorbed into the systemic circulation. Further, if the drug is taken orally, all of the drug must pass through the liver prior to reaching the systemic circulation. Although nalmefene is not subject to substantial first pass metabolism, some metabolism of the drug would occur. Part of this metabolism can be avoided by administering the drug via a suppository thus providing a greater effect per amount of the drug administered. In addition, it should be pointed out that administration via a suppository can be carried out relatively simply and accurately without restrictions as to time of administration. Administration can be effected even during nausea, vomiting or unconsciousness or after surgical operation. For these reasons, the administration of nalmefene via a rectal suppository for the prevention of SIDS is believed to be the most practical means of administration.

While the present invention has been described in detail with reference to specific embodiments thereof, it will be apparent to one skilled in the art that various changes and modifications can be made therein without departing from the spirit and scope thereof.

What is claimed is:

1. A method aiding in the prevention of SIDS, comprising:
   administering a pharmaceutically effective amount of 6-methylene-6-desoxy-N-cyclopropylmethyl-14-hydroxydihydronormorphone to an infant determined to be susceptible to SIDS so as to block the attachment of endogenous endorphins to nerve receptor sites responsible for the actuation of respiration.

2. A method of aiding in the prevention of SIDS as claimed in claim 1, wherein the 6-methylene-6-desoxy-N-cyclopropylmethyl-14-hydroxydihydronormorphone is administered via the GI track of the infant.

3. A method of aiding in the prevention of SIDS as claimed in claim 2, wherein the 6-methylene-6-desoxy-N-cyclopropylmethly-14-hydroxydihydronormorphone is administered orally.

4. A method of aiding in the prevention of SIDS as claimed in claim 2, wherein the 6-methylene-6-desoxy-N-cyclopropylmethyl-14-hydroxydihydronormorphone is administered anally.

5. A method of aiding in the prevention of SIDS as claimed in claim 1, wherein the 6-methylene-6-desoxy-N-cyclopropylmethyl-14-hydroxydihydronormorphone is administered on a bi-daily basis.

6. A method of aiding in the prevention of SIDS as claimed in claim 5, wherein the 6-methylene-6-desoxy-N-cyclopropylmethyl-14-hydroxydihydronormorphone is administered in an amount in the range of 0.01 to 0.5 mg/kg of body weight.

7. A method of aiding in the prevention of SIDS as claimed in claim 6, wherein the 6-methylene-6-desoxy-N-cyclopropylmethyl-14-hydroxydihydronormorphone is administered in an amount of about 0.1 mg/kg.

* * * * *